(12) United States Patent
Khoshdel

(10) Patent No.: US 6,730,289 B2
(45) Date of Patent: May 4, 2004

(54) COSMETIC COMPOSITION

(75) Inventor: Ezat Khoshdel, Bebington (GB)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

(21) Appl. No.: 10/055,829

(22) Filed: Jan. 23, 2002

(65) Prior Publication Data

US 2002/0176837 A1 Nov. 28, 2002

(30) Foreign Application Priority Data

Jan. 23, 2001 (GB) .............................. 0101736

(51) Int. Cl.$^7$ ................................. A61K 7/11
(52) U.S. Cl. .................... 424/47; 424/70.1; 424/70.11; 424/401
(58) Field of Search .............................. 424/70.1, 70.11, 424/401, 47

(56) References Cited

U.S. PATENT DOCUMENTS 5,968,494 A 10/1999 Kukkala et al.
6,132,704 A 10/2000 Bhatt et al.

FOREIGN PATENT DOCUMENTS

| EP | 0442652 | 8/1991 |
| EP | 0838212 A1 | 4/1998 |
| EP | 0937451 A2 | 8/1999 |
| FR | 1116759 | 12/1952 |
| GB | 1237339 | 6/1971 |
| WO | 87/00851 | 2/1987 |
| WO | 92/13018 | 8/1992 |
| WO | 94/13724 | 6/1994 |

OTHER PUBLICATIONS

RU abstract2097017(1997).*
JP 55080455A assigned to Sanyo 6/80.

* cited by examiner

Primary Examiner—Jyothsna Venkat
(74) Attorney, Agent, or Firm—Michael P. Aronson

(57) ABSTRACT

The present invention relates to carbamate group modified polyurethanes and a process for preparing carbamate group modified polyurethanes comprising reacting a polyurethane polymer with an alkylating or an acylating agent. The invention also relates to cosmetic or personal care compositions comprising (i) a styling polymer comprising a carbamate group modified polyurethane and (ii) a cosmetically acceptable diluent or carrier.

9 Claims, No Drawings

COSMETIC COMPOSITION

FIELD OF THE INVENTION

This invention relates to polymers for use in cosmetic and personal care compositions, methods of producing the polymers, cosmetic and personal care compositions containing them, and to a method of treating hair using the compositions. More particularly, the invention relates to carbamate group modified polyurethanes, methods of producing these polyurethanes and hair styling compositions such as hair fixative compositions that contain carbamate group modified polyurethanes, and their use.

BACKGROUND AND PRIOR ART

The desire to have the hair retain a particular shape or style is widely held. The most common approach for accomplishing styling of hair is the application of a composition to dampened hair, after shampooing and/or conditioning, or to dry, styled hair. These compositions provide temporary styling benefits and can readily be removed by water or shampooing. To date, the materials employed in the hair care compositions to provide styling benefits have generally been natural or synthetic resins and have been applied in the form of, for example, sprays, mousses, gels and lotions.

Recently, it has become desirable to provide a high level of style retention, or strong hold, from a hair spray composition. In a typical hair spray, hold is achieved by the use of commercially available styling polymers, such as AMPHOMER(TM), supplied by National Starch Chemical Company, LUVIMER(TM), supplied by BASF, GANTREZ (TM), supplied by ISP Chemicals and also silicone graft copolymers, supplied by Mitsubishi Chemicals.

In addition to providing a high degree of hold to hair, hair fixative compositions must meet other performance requirements. For example, hair fixative compositions should maintain a high degree of gloss, curl retention, stiffness and humidity resistance, whilst also having pleasing aesthetics with a natural soft feel, no adhesive tackiness, no brittle feel and no flake development. Hair fixative compositions must also be readily removable from the hair.

Typically, the styling polymers have a carbon backbone comprising various hydrophilic and hydrophobic vinylic monomers. These polymers can be nonionic or they can carry a charge, usually a negative charge. The hydrophilic monomer is employed to render the polymer water-soluble and the hydrophobic monomer is generally selected to enhance humidity resistance of the styling resins. Traditionally, the anionically charged resins are formed from the corresponding acids (neutralised) using alkalising agents such as sodium or potassium hydroxide as well as certain functional amines such as aminomethyl propanol (AMP) to tailor their solubility and film forming properties.

The hydrophobic/hydrophilic character of modern styling resins is carefully balanced to produce materials that are soluble in hydroalcoholic solvents, typically 80% volatile organics content (VOC). To improve the performance of modern styling products even further, non-volatile plasticisers such as propylene glycol, dipropylene glycol, acetyl tri-n-butyl citrate and acetyl tri-2-ethoxyhexyl citrate (Citroflex(TM)) have been employed in the compositions.

In addition to styling polymers, hair fixative compositions contain a delivery system. The delivery system is typically an alcohol or a mixture of alcohol and water. Aerosol delivery compositions typically also contain a propellant, such as a volatile hydrocarbon. Alternative delivery systems for hair fixative compositions have also been developed, for example pump sprays, gels and mousses.

Conventional hair styling compositions require a relatively high content of volatile organic compounds (VOCs) in order to solubilise the hair styling polymer. However, delivery systems comprising alcohol and hydrocarbons are becoming less acceptable. This is due to environmental regulations controlling the emission of volatile organic compounds (VOCs) into the atmosphere. It is, therefore, desirable for economic and environmental reasons to reduce the VOC of hair styling compositions.

The use of polyurethanes as hair styling polymers in aqueous or low VOC compositions has been investigated. By the term "low VOC compositions" we mean compositions comprising 80% or less VOCs.

Polyurethanes are a class of polymers that contain carbamate groups (—NHCOO—) in their backbone structure. Carbamate groups are also referred to as urethane groups. Polyurethanes are typically produced by the reaction of a diisocyanate with a polymeric diol (a polyol), or a combination of polyols, and a short chain diol extender. The polyols are typically polyethers or polyesters or a combination of both. The generic molecular structure of segmented polyurethane obtained from the polymerisation of a diisocyanate, a polyol and a simple alkane-diol extender carrying a charged group can be represented as follows:

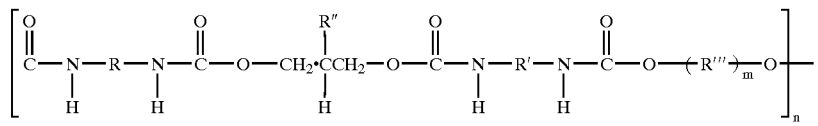

wherein R and R' are independently an optionally substituted arylene, alkylene, cycloalkylene, alkenylene, or alkynylene group, R" is a charge carrying functional group such as carboxylate, sulphate, phosphate, a quaternary ammonium group or a phosphonium group and R'" represents a polymeric chain representing a polymeric diol, usually a polyether, e.g., polyethyleneglycol, polypropyleneglycol and their copolymers, polytetrahydrofuran or an oligomeric aliphatic/aromatic polyester. m and n are positive integers.

U.S. Pat. No. 5,968,494 and EP-A-937451, both describe the preparation and use of polyurethanes with carboxylate functionality for hair fixative applications.

DE-A-4241118 describes the use of cationic polyurethanes and polyureas as auxiliaries in cosmetic and pharmaceutical preparations.

U.S. Pat. No. 6,132,704 discloses carboxylated urethane resins for use in hair styling gels. The resins contain pendant carboxyl groups.

However, although polyurethanes and polyureas display hair fixative properties, they adhere to hair so strongly that it is generally not possible to remove them using conventional methods such as shampooing. Even after repeated shampooing the polymer can be felt on hair. This leads to accumulation and build-up problems on hair with perceived negative sensory effects.

Without wishing to be bound by theory, the present applicants believe that the difficulty in removing polyurethanes from hair may be due to the formation of hydrogen bonds between the carbamate groups of polyurethane and the amide groups that are present in hair fibres.

Various attempts have previously been made to improve the removal of polyurethanes from hair. These have generally been unsuccessful. For example, it has been found that increasing the acid content of polyurethanes in order to increase their solubility in aqueous systems whilst employing certain alkali or amine neutralisers has not provided polymers that can be removed from hair by washing.

Thus, there is a need for improved hair styling polymers that are soluble or dispersible in aqueous or low VOC compositions and which can be relatively easily removed from the hair by washing. The hair styling polymers must also provide the desired hair styling properties, such as low tack polymer film characteristics, improved hold of the hair, and/or enhanced shine of hair and/or better natural movement of hair. Current styling polymers and hair fixative compositions do not provide this required balance of properties. The present invention seeks to solve this problem.

Carbamate polymers are known to be useful in other applications. For example, GB 1237339 and WO 87/00851 disclose N-alkylated polyurethanes for use as foam crash pads and coating compositions, respectively. There is no mention in either document of N-acylated polymers. Similarly, JP-A-55080455 discloses coating compositions comprising a polyurethane, an acid compound and a tertiary amine.

SUMMARY OF THE INVENTION

The present invention in a first aspect, therefore, provides a cosmetic or personal care composition comprising:
(i) a styling polymer comprising a carbamate group modified polyurethane comprising units having the formula:

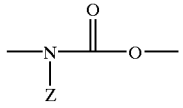

wherein Z is hydrogen, an alkyl, fully or partially fluorinated alkyl or acyl group, provided that not all of the Z groups in the polyurethane are hydrogen; and
(ii) a cosmetically acceptable diluent or carrier.

The present invention also provides in a second aspect a process for the preparation of carbamate group modified polyurethanes of the first aspect of the invention, which process comprises reacting a polyurethane polymer with an alkylating or an acylating agent.

The present invention further provides a carbamate group modified polyurethane comprising units having the formula:

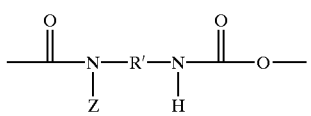

wherein R' is a substituted or unsubstituted arylene, alkylene, cycloalkylene, alkenylene, or alkynylene group, and the polymer has a net positive or negative charge and Z is acyl.

In another aspect, the invention provides the use of a modified polyurethane of the first aspect of the invention or a composition of the invention for the cosmetic treatment of hair.

In another aspect, the invention provides the use of a modified polyurethane of the invention as a hair styling polymer.

DETAILED DESCRIPTION OF THE INVENTION

The present invention involves carbamate group modified polyurethanes comprising units having the formula:

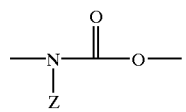

wherein Z is hydrogen, an alkyl, fully or partially fluorinated alkyl or acyl group, provided that not all of the Z groups in the polyurethane are hydrogen.

In a preferred embodiment, the polyurethane further comprises units having the formula:

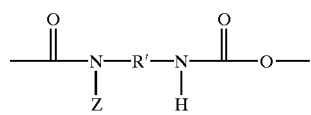

wherein R' is a substituted or unsubstituted arylene, alkylene, cycloalkylene, alkenylene, or alkynylene group.

Preferably, the polyurethane has a net positive or negative charge and, more preferably, comprises units having the formula:

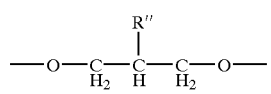

wherein R" comprises a group having a positive or negative charge, for example carboxylate, sulphate, phosphate, a quaternary ammonium group or a phosphonium group. Preferably, R" represents carboxylate, sulphate, phosphate, a quaternary ammonium group or a phosphonium group or an aryl, alkyl, arylalkyl, cycloalkyl, alkenyl, or alkynyl group substituted with one or more groups selected from carboxylate, sulphate, phosphate, quaternary ammonium and phosphonium groups or mixtures thereof.

The polymer may further comprise groups of the formula —O—(R"")—O— wherein R"" is a polymeric group selected from polyethers, polyesters and polyether/polyester copolymers. Polyethers include, for example, poly(ethylene glycol) and poly(propylene glycol). Polyesters include, for example, poly(ethylene terephthalate).

In a most preferred embodiment, the carbamate group modified polyurethanes of the invention comprise repeating units having the formula:

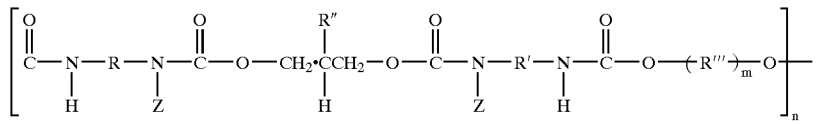

wherein R, R', R", and Z are as defined above and R'" is a repeating unit for polymer R"", provided that not all of the Z groups in the polyurethane are hydrogen, and n and m are positive integers. Preferably, n has a value of from 2 to 100,000, more preferably from 5 to 50,000 and/or m has a value of from 1 to 10,000.

In principle, any chemical modification that can reduce the number of protons on the carbamate groups will reduce the wash-off problem. However, full modification of the polyurethanes may result in loss of film forming properties and hence reduced polymer performance. Therefore, in the polyurethanes of the present invention, not all of the Z groups are hydrogen i.e., at least a proportion of the Z groups are other than hydrogen.

By the term "alkyl", we include straight chain and, for alkyl groups containing three or more carbon atoms, branched groups. The term "alkylene" is defined similarly to the term "alkyl" but represents a divalent radical.

The terms "alkenyl" and "alkynyl" are defined similarly to the term "alkyl" and the terms "alkenylene" and "alkynylene" are defined similarly to the term "alkylene" but the groups contain one or more carbon-carbon double or triple bonds, respectively. The term "aryl" includes phenyl, optionally substituted, with for example from one to five alkyl groups. The term "arylene" is defined similarly to the term "aryl" but refers to divalent radicals.

The term "arylalkyl" means alkyl substituted with aryl, such as benzyl.

Preferably, the alkyl, alkenyl, alkynyl, alkylene, alkenylene or alkynylene groups contain from 1 to 24 carbon atoms, more preferably from 1 to 12 carbon atoms and even more preferably from 1 to 6 carbon atoms.

Preferred straight chain alkyl groups include methyl, ethyl, propyl, butyl, pentyl and hexyl. Preferred branched alkyl groups include isopropyl, isobutyl and tert-butyl. Preferred straight chain alkylene groups include methylene, ethylene, propylene, butylene, pentylene and hexylene. Preferred branched alkyl groups include isopropylene, isobutylene and tert-butylene.

Preferred substituents for the alkyl, alkenyl, alkynyl, alkylene, alkenylene and alkynylene groups include aryl substituents.

Preferably, the cycloalkyl or cycloalkylene groups contain from 3 to 8 carbon atoms in the cyclic ring.

Preferably, the aryl or arylene groups contain from 6 to 10 carbon atoms.

Preferably, the acyl groups contain from 1 to 24 carbon atoms, more preferably from 1 to 12 carbon atoms and even more preferably from 1 to 6 carbon atoms.

It is most preferred that Z is an acetyl group.

The modified polyurethane polymers of the invention preferably comprise from 0.001% to 5% (more preferably from 0.1% to 1%, most preferably from 0.2% to 0.5%) by weight of the polymer of Z groups which are alkyl, fully or partially fluorinated alkyl or acyl groups (more preferably acetyl groups), the remaining Z groups being hydrogen.

Preferred polymers are obtainable by the reaction of acetic anhydride with polyurethane in an amount of from 0.01% to 5% by weight of acetic anhydride based on weight of polyurethane.

The carbamate group modified polyurethane may be used for the cosmetic treatment of hair, preferably as a hair styling polymer.

The process for the preparation of carbamate group modified polyurethanes according to the invention comprises reacting a polyurethane polymer with an alkylating or an acylating agent.

Known commercial or non-commercial hydrophilic polyurethanes can be modified using this process.

Suitable alkylating or acylating agents include alkyl halides, aryl halides, arylalkyl halides, partially fluorinated alkyl halides, partially fluorinated aryl halides, partially fluorinated arylalkyl halides, acid halides, acid anhydrides, mixed acid anhydrides, N-carboxy anhydrides, lactones, azlactones and thiolactones.

Anhydrides suitable for use in the process of the present invention include acetic anhydride, citric anhydride, tartaric anhydride, maleic anhydride, succinic anhydride, citraconic anhydride, itaconic anhydride, trifluoroacetic anhydride, (±)-camphoric acid anhydride, (±)-1,8,8-trimethyl-3-oxabicyclo[3.2.1]octane-2,4-dione, (+)-di-O-acetyl-L-tartaric anhydride, (+)-diacetyl-L-tartaric anhydride, (2-dodecen-1-yl)succinic anhydride, (2-nonen-1-yl)succinic anhydride, (R)-(+)-2-acetoxysuccinic anhydride, (S)-(+)-2-methylbutyric anhydride, (S)-(−)-1,2,3,4-tetrahydro-2,3-isoquinolinedicarboxylic anhydride, (S)-(−)-2-(trifluoroacetamido)succinic anhydride, N-trifluoroacetyl-L-aspartic acid anhydride, (S)-(−)-2-acetoxysuccinic anhydride, (S)-(−)-2-formamidosuccinic anhydride, (R)-2-acetoxysuccinic anhydride, O-acetyl-D-malic anhydride, (S)-2-acetoxysuccinic anhydride and O-acetyl-L-malic anhydride.

Preferably, the acylating agent is acetic anhydride. When the acylating agent is acetic anhydride, a carbamate-modified polyurethane comprising the following groups is provided:

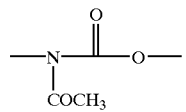

In a preferred embodiment, a polyurethane having the following formula is provided:

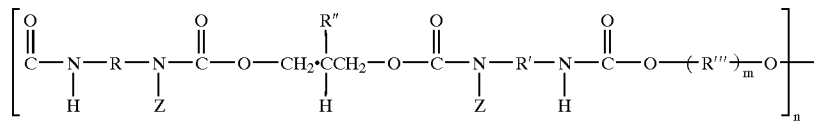

where R, R', R", R''', and n have the same meaning as above and at least a proportion of the Z groups are acetyl, the other Z groups being hydrogen.

The process of the present invention is preferably conducted at a temperature of from 20° C. to 100° C., more preferably about 60° C.

Cosmetic or personal care compositions according to the invention comprise (i) a styling polymer comprising a carbamate group modified polyurethane and (ii) a cosmetically acceptable diluent or carrier.

The cosmetic or personal care composition is preferably a hair styling composition. The composition may be used for the cosmetic treatment of hair.

The compositions of the present invention can be removed from the hair by washing. Without wishing to be bound by theory, it is thought that the carbamate group modified polyurethanes are easier to remove from the hair because fewer hydrogen bonds can form between the hair and the polyurethane backbone. This is because, compared to typical polyurethanes, carbamate group modified polyurethanes have fewer protons available for hydrogen bonding.

The compositions of the present invention preferably comprise the carbamate group modified polyurethane in an amount of from 0.01 to 10% by weight, more preferably in an amount of from 0.1 to 10% by weight, of the total composition. An especially preferred composition comprises from 0.5% to 10%, even more preferably from 0.75% to 6% by weight, of the total composition of the carbamate group modified polyurethane.

The polyurethane may also include grafted silicone, such as polydimethylsiloxane. Preferably, the compositions of the invention comprise from 0.01% to 10%, more preferably from 0.01% to 5%, by weight silicone, based on the total weight of the composition.

With certain of the hair styling carbamate group modified polyurethanes it may be necessary to neutralise some acidic groups to promote their solubility and dispersibility in water. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001% to about 10% by weight of the total composition.

As well as the carbamate group modified polyurethane styling polymer, the compositions of the present invention may additionally comprise one or more additional styling polymers.

Hair styling polymers are well known. Suitable additional styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Examples of anionic hair styling polymers are:
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers. The additional styling polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ® ES series available from ISP Corporation esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as additional styling polymers in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macro-grafted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

Preferred additional styling polymers for use in the compositions of the invention comprise one or more of the same or different hydrophobic groups. The hydrophobic groups are preferably selected from: $C_1$–$C_{24}$ alkyl, $C_1$–$C_{24}$ alkenyl or $C_1$ to $C_{24}$ alkynyl; $C_1$–$C_{24}$ alkyl, $C_1$–$C_{24}$ alkenyl or $C_1$–$C_{24}$ alkynyl, each of the latter three groups being optionally substituted with aryl, and mixtures thereof.

The cosmetically acceptable diluent or carriers used in the compositions of the invention must be suitable for application to the hair. By the phrase "suitable for application to hair" we mean that the carrier does not damage or negatively affect the aesthetics of hair or cause irritation to the underlying skin.

Preferably, the diluent or carrier is present at from 0.5% to 99.5%, more preferably from 5.0% to 99.5%, even more preferably from 10.0% to 98.0%, by weight of the composition.

Carriers suitable for use in the hair care compositions of the present invention include, for example, those used in the formulation of hair sprays, mousses, tonics, gels, shampoos, conditioners and rinses. The choice of appropriate carrier will also depend on the particular composition to be used, and on whether the product formulated is meant to be left on the surface to which it is applied (e.g. hair spray, mousse, tonic or gel) or rinsed off after use (e.g. shampoo, conditioner, rinse).

A person skilled in the art would be able to select the carriers and additional components required to formulate cosmetic and personal care compositions of the invention.

The diluents and carriers used in the compositions of the invention may include a wide range of components conventionally used in hair care compositions. The carriers can contain a solvent to dissolve or disperse the particular composition being used, with water, the $C_1$–$C_6$ alcohols, the $C_1$–$C_6$ alkyl acetates and mixtures thereof being preferred. The carriers can also contain a wide variety of additional materials such as acetone, hydrocarbons (such as isobutane, hexane and decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Suitable spray containers are well known in the art and include conventional, non-aerosol pump sprays, such as "atomisers", aerosol containers or cans having propellant, as described above, and also pump aerosol containers utilising compressed air as the propellant. Where the hair care compositions are conditioners and rinses, the carrier can include a wide variety of conditioning materials. Where the hair care compositions are shampoos, the carrier can include, for example, surfactants, suspending agents and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, for example from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g. mineral oil, ethanol, isopropanol, dimethicone, cyclomethicone, and the like); aqueous-based single phase liquid solvents (e.g. hydro-alcoholic solvent systems); and thickened versions of these anhydrous and aqueous-based single phase solvents (e.g. where the viscosity of the solvent has been increased to form a solid or semi-solid by the addition of appropriate gums, resins, waxes, polymers, salts, and the like).

The compositions of the present invention preferably comprise, amongst other carriers, water and ethanol, with the amount of water being preferably at least 20% by weight of the composition, more preferably at least 40% by weight (such as at least 50% by weight), more preferably at least 60% by weight, more preferably at least 70% by weight, even more preferably at least 80% by weight of the composition. The ratio of water to organic solvent (including, for example, ethanol) may preferably vary from 1:4 to 10:1, more preferably 1:1 to 10:1, most preferably 2:1 to 10:1. The compositions may, alternatively, contain water as the only solvent i.e. have a VOC of 0%.

Compositions of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like.

A particularly preferred composition according to the invention is a hair spray composition comprising:
  (i) from 0.01% to 10% (more preferably from 0.1% to 10%) by weight of a carbamate group modified polyurethane;
  (ii) optionally, from 0.001% to 10% (more preferably from 0.01% to 5%) by weight of a neutraliser;
  (iii) optionally, from 0.01% to 5% by weight of a silicone;
  (iv) at least 20% (more preferably at least 50%) by weight water; and
  (v) up to 50% by weight of a propellant.

A wide variety of additional components can be employed in cosmetic and personal care compositions according to the present invention. The additional components used in a particular composition will vary with product type and can be routinely chosen by one skilled in the art. Examples of suitable additional components include the following:
  a perfume or fragrance, for example in an amount of from 0.01% to 1% by weight of the total composition.
  sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
  anti-dandruff actives such as zinc pyrithione, piroctone olamine, selenium disulphide, sulphur, coal tar, and the like.
  hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.
  surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.
  carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10–C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.
  emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.
  vitamins and derivatives thereof (e.g., ascorbic acid, vitamin E, tocopheryl acetate, retinoic acid, retinol, retinoids, and the like).
  cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).
  preservatives, antioxidants, chelators and sequestrants; and aesthetic components such as fragrances, colourings, hair nutrients and essential oils.

The following non-limiting Examples further illustrate the preferred embodiments of the invention. All percentages

EXAMPLES

Example 1 Preparation of Carbamate Group Modified Polyurethanes

The commercially available polyurethane, Luviset PUR, (available from BASF Chemicals Company) was modified with varying amounts of acetic anhydride according to the following procedure.

Luviset PUR is a clear liquid, supplied as a solution of 30% polymer, 10% ethanol and 60% water. The polymer is anionic, 100% neutralised and soluble in ethanol/water mixtures at pH values of 8 or above.

The water and ethanol were removed from the Luviset PUR product by rotary evaporation and overnight drying in a vacuum oven to provide the polyurethane.

Polyurethane (30 g) was dissolved in tetrahydrofuran (100 ml) and to this solution acetic anhydride (0.05 ml) was added. The reaction mixture was heated at 60° C. for 4 hours. The solvent was then removed using a rotary evaporator. The polymer was finally dried in vacuum oven overnight at 40° C. to give a white, crystalline material (modified polyurethane-1).

The procedure was then repeated using different amounts of acetic anhydride as follows:

| Sample | Volume of Acetic Anhydride |
| --- | --- |
| Modified polyurethane-2 | 0.1 ml |
| Modified polyurethane-3 | 0.2 ml |
| Modified polyurethane-4 | 0.3 ml |
| Modified polyurethane-5 | 0.4 ml |

The appearance of a band around 1.98 ppm in the $^1$H NMR spectra of all of the modified polyurethanes corresponds to the $CH_3$ group of the acetylated product. The intensity of this band increases as the level of acetylation is increased. This band is not present in the unmodified polyurethane.

Example 2 Solubility of Carbamate Group Modified Polyurethanes 1 to 5

The solubility of a sample (0.2 g) of each of the carbamate group modified polyurethanes 1 to 5 from Example 1 was tested. The results are shown in Tables 1 to 5 below.

TABLE 1

Solubility Tests on Modified Polyurethane-1 (MP-1)

| Volume of water (ml) | Volume of ethanol (ml) | Volume of acetone (ml) | Volume of diethyl ether (ml) | Comment |
| --- | --- | --- | --- | --- |
| — | 10 | — | — | Soluble and clear |
| — | 20 | — | — | Soluble and clear |
| — | 30 | — | — | Soluble and clear |
| 10 | — | — | — | Insoluble |
| 20 | — | — | — | Insoluble |
| 30 | — | — | — | Insoluble |
| — | — | — | 10 | Insoluble |
| — | — | 10 | — | Soluble |

TABLE 2

Solubility Tests on Modified Polyurethane-2 (MP-2)

| Volume of water (ml) | Volume of ethanol (ml) | Volume of acetone (ml) | Volume of diethyl ether (ml) | Comment |
| --- | --- | --- | --- | --- |
| — | 10 | — | — | Soluble and clear |
| — | 20 | — | — | Soluble and clear |
| — | 30 | — | — | Soluble and clear |
| 10 | — | — | — | Insoluble |
| 20 | — | — | — | Insoluble |
| 30 | — | — | — | Insoluble |
| — | — | — | 10 | Insoluble |
| — | — | 10 | — | Soluble |

TABLE 3

Solubility Tests on Modified Polyurethane-3 (MP-3)

| Volume of water (ml) | Volume of ethanol (ml) | Volume of acetone (ml) | Volume of diethyl ether (ml) | Comment |
| --- | --- | --- | --- | --- |
| — | 3 | — | — | Completely insoluble |
| 10 | — | — | — | Insoluble |
| — | 0.7 | — | — | Soluble and clear |
| — | — | 1 | — | Soluble and clear |
| — | — | — | 10 | Insoluble |

TABLE 4

Solubility Tests on Modified Polyurethane-4 (MP-4)

| Volume of water (ml) | Volume of ethanol (ml) | Volume of acetone (ml) | Volume of diethyl ether (ml) | Comment |
| --- | --- | --- | --- | --- |
| — | 3 | — | — | Soluble and clear |
| — | 0.7 | — | — | Difficult soluble |
| — | — | 1 | — | Soluble |
| 10 | — | — | — | Insoluble |
| — | — | — | 10 | Insoluble |

TABLE 5

Solubility Tests on Modified Polyurethane-5 (MP-5)

| Volume of water (ml) | Volume of ethanol (ml) | Volume of acetone (ml) | Volume of diethyl ether (ml) | Comment |
| --- | --- | --- | --- | --- |
| — | 3 | — | — | Soluble and clear |
| — | 0.7 | — | — | Difficult to solubilise |
| — | — | 1 | — | Partially soluble |
| 10 | — | — | — | Insoluble |
| — | — | — | 10 | Insoluble |

Example 3

The ease of removal of modified polyurethane-2 from hair by washing compared to pure polyurethane was tested. Both polyurethanes were neutralised by 90% with 2-amino-2-methyl-1-propanol.

The modified polyurethane-2 displayed was washed off the hair more easily than the pure polyurethane. Other attributes, such as smoothness, softness and ease of comb were not affected. Thus, the modified polyurethanes can be readily removed from the hair by shampooing and also provide the desired properties to the hair.

Examples 4 to 9

The following are examples of compositions according to the invention.

The materials in the examples include the following:

| Material | Supplier | Function |
|---|---|---|
| Silicone emulsion X2 1787 ™ | Dow Corning | conditioning |
| VOLPO CS 50 ™ | Croda Chemicals | surfactant |
| Sepicide LD ™ | Seppic | preservative |
| Cremophor RH410 ™ | BASF | stabiliser |
| Silicone DC 200/DC 24 S ™ | Dow Corning | conditioning |
| Silwet L7602/L-720 ™ | Union Carbide | surfactant |
| CAP 40 ™ | Calor Gas | propellant |
| Carbopol 980 ™ | B F Goodrich | structurant |
| Jaguar HP-105 ™ | Rhodia | conditioning |
| Silicone Fluid 245 ™ | Dow Corning | conditioning |

Ethanol is SD Alcohol 40-B (92% active)

Example 4

A styling mousse is formulated as follows:

| Material | % in product (w/w) |
|---|---|
| Silicone Emulsion X2 1787 | 1.2 |
| Polymer of the invention | 1.5 |
| VOLPO CS 50 | 0.3 |
| Sepicide LD | 0.4 |
| Cremophor RH410 | 0.2 |
| Ethanol | 7.5 |
| CAP 40 | 8.0 |
| Perfume | 0.2 |
| Water | to 100% |

Example 5

A hairspray is formulated as follows:

| Material | % in product (w/w) |
|---|---|
| Polymer of the invention | 3.0 |
| Silicone DC200 | 0.09 |
| Silwet L7602 | 0.09 |
| CAP 40 | 35.0 |
| Ethanol | 60.0 |
| Perfume | 0.10 |
| Water | to 100% |

Example 6

A pump spray is formulated as follows:

| Material | % w/w |
|---|---|
| Ethanol | 60.0 |
| Polymer of the invention | 3.5 |
| Silwet L-720 | 0.3 |
| Silicone DC24S | 0.15 |
| Fragrance | 0.3 |
| Water | to 100% |

Example 7

A styling gel is formulated as follows:

| Material | % w/w |
|---|---|
| Polymer of the invention | 3.8 |
| Carbopol 980 | 0.4 |
| Water | to 100% |
| Sepicide LD | 0.4 |
| Sodium hydroxide (8% 2M) | 0.1 |
| Ethanol | 10.0 |
| Cremaphor RH410 | 0.4 |
| Jaguar HP-105 | 0.2 |
| Perfume | 0.15 |

Example 8

A 55% voc propelled aerosol composition is formulated as follows:

| Material | % w/w |
|---|---|
| Polymer of the invention | 3.75 |
| Silicone Fluid 245 | 0.20 |
| Fragrance | 0.32 |
| Ethanol | 19.53 |
| Dimethyl ether | 35.00 |
| Sodium benzoate | 0.26 |
| Cyclohexylamine | 0.21 |
| Water | to 100% |

Example 9

A 55% voc pump hairspray composition is formulated as follows:

| Material | % w/w |
|---|---|
| Polymer of the invention | 3.75 |
| Cyclopentasiloxane (99% active) | 0.15 |
| Benzophenone 4 | 0.0001 |
| Fragrance | 0.25 |
| Ethanol | 58.00 |
| Water | to 100% |

Example 10—Variation of Properties with Degree of Acetylation

The percentage by weight modification of the polyurethanes-1 to −5 is given in the following table.

TABLE 1

| | Modification of PUR with acetic anhydride | | | |
|---|---|---|---|---|
| Polyurethane No. | Polyurethane (g) | Acetic Anhydride ml | g | % Modification |
| 1 | 30 | 0.05 | 0.054 | 0.18 |
| 2 | 30 | 0.1 | 0.016 | 0.36 |
| 3 | 30 | 0.2 | 0.216 | 0.71 |

TABLE 1-continued

Modification of PUR with acetic anhydride

| Polyurethane No. | Polyurethane (g) | Acetic Anhydride ml | Acetic Anhydride g | % Modification |
|---|---|---|---|---|
| 4 | 30 | 0.3 | 0.324 | 1.07 |
| 5 | 30 | 0.4 | 0.432 | 1.42 |

The appearance of a band around 1.98 ppm NMR spectra of the modified polyurethanes corresponded to $CH_3$ group of the acetylated product. The intensity of this band increased as we increase the level of acetylation. This band was not present in un-modified polyurethane.

The modified polyurethanes, together with an unmodified material were neutralised between 30–100% with AMP and applied to hair switches. The switches were washed with salon C shampoo and tested by a specialist panel. The panellists ranked the hair switches on the basis of their performance, ranging from 5 as the best and 1 as the worst. The results show that the optimum level of modification was achieved with the addition of 0.1 ml (0.36 wt %) of acetic anhydride.

AFM images revealed that there were no deposits on hair when treated with modified polyurethanes. On the other hand, deposits of the un-modified polyurethanes could be seen on treated hair.

Viscosity and bond strength of the modified polyurethanes were similar to those of unmodified material, indicating no significant effect/change on polymer microstructure.

What is claimed is:

1. A cosmetic or personal care composition comprising:
   (i) a hair styling polymer comprising a polyurethane polymer that has been modified by replacing a portion of the hydrogen atoms that are attached to the nitrogen atom of the carbamate group by an acyl group having 1–6 carbon atoms; and
   (ii) a cosmetically acceptable diluent or carrier comprising at least 20% water by weight of the composition.

2. A composition according to claim 1, which is obtainable by the reaction of acetic anhydride with a polyurethane in an amount of from 0.01% to 5% by weight of acetic anhydride based on weight of polyurethane.

3. A composition according to claim 1, which further comprises a perfume or fragrance.

4. A composition according to claim 1, wherein the modified polyurethane is present in the composition in an amount of from 0.01 to 10% by weight.

5. A composition according to claim 4, wherein the modified polyurethane is present in an amount of from 0.75 to 6% by weight.

6. A composition according to claim 1, further comprising one or more additional styling polymers.

7. A composition according to claim 1, wherein the cosmetically acceptable diluent or carrier further comprises at least one solvent selected from the group consisting of a $C_1$ to $C_6$ alcohol, a $C_1$ to $C_6$ alkyl acetate and mixtures thereof.

8. A composition according to claim 7, wherein the solvent is ethanol.

9. A cosmetic method for the treatment of hair which comprises applying to the hair a modified polyurethane composition as defined in claim 1.

* * * * *

UNITED STATES PATENT AND TRADEMARK OFFICE
CERTIFICATE OF CORRECTION

PATENT NO. : 6,730,289 B2
DATED : May 4, 2004
INVENTOR(S) : Ezat Khoshdel

It is certified that error appears in the above-identified patent and that said Letters Patent is hereby corrected as shown below:

Column 18,
Line 7, change "1—6 carbon atoms; and" to -- 1—6 carbon atoms wherein the polyurethane polymer is consisting of diisocyanate, isophthalic acid, adipic acid, hexane diol, neopentylglycol, dimethylol propionic acid and quencher; and --

Signed and Sealed this

Sixth Day of July, 2004

JON W. DUDAS
*Acting Director of the United States Patent and Trademark Office*